United States Patent [19]

Ralph et al.

[11] Patent Number: 5,607,426
[45] Date of Patent: Mar. 4, 1997

[54] THREADED POLYAXIAL LOCKING SCREW PLATE ASSEMBLY

[75] Inventors: James D. Ralph, Oakland; Steve Tatar, Montville, both of N.J.

[73] Assignee: Fastenletix, L.L.C., Summit, N.J.

[21] Appl. No.: 606,221

[22] Filed: Feb. 23, 1996

Related U.S. Application Data

[63] Continuation-in-part of Ser. No. 421,087, Apr. 13, 1995, Pat. No. 5,520,690.

[51] Int. Cl.⁶ .................................................. A61B 17/70
[52] U.S. Cl. .............................. 606/61; 606/69; 606/70; 606/73
[58] Field of Search ........................ 606/61, 60, 69, 606/70, 71, 72, 73, 75, 76, 104; 623/16, 17

[56] References Cited

U.S. PATENT DOCUMENTS

| | | | |
|---|---|---|---|
| 5,053,036 | 10/1991 | Perren et al. | 606/69 |
| 5,057,111 | 10/1991 | Park | 606/69 |
| 5,147,361 | 9/1992 | Ojima et al. | 606/61 |
| 5,180,381 | 1/1993 | Aust et al. | 606/61 |
| 5,269,784 | 12/1993 | Mast | 606/69 |
| 5,324,290 | 6/1994 | Zdeblick et al. | 606/61 |
| 5,429,639 | 7/1995 | Judet | 606/61 |

FOREIGN PATENT DOCUMENTS

| | | | |
|---|---|---|---|
| 9416634 | 8/1994 | WIPO | 606/69 |

OTHER PUBLICATIONS

"Cervi–Lok Cervical Fixation System", Spinetech, Inc. 980 E. Hennepin Ave., Minneapolis, MN 55414, 1994.
"System Overview–Axis Fixation System", Sofamor Danek, 1800 Pyramid Place, Memphis, TN 38132, 1994.
"Surgical Technique–Orion Anterior Cervical Plate System" Sofamor Danek, Memphis, TN 38132, 1994.
"Surgical Technique–ZPlate–ATL Anterior Fixation System" Sofamor Danek, Memphis TN 38132, 1994.

*Primary Examiner*—Guy V. Tucker
*Attorney, Agent, or Firm*—Joseph P. Errico

[57] ABSTRACT

The present invention is a polyaxial locking screw plate assembly for immobilization of vertebral bones, via fixation to surfaces thereof. The invention includes a plate, having an upper portion and a lower portion, each of which has a pair of holes having a threaded upper portion and a tapered lower portion. Coupling elements, including slideably joined socket and cap portions, are mounted about the semi-spherical heads of bone screws, which are screwed through the holes in the plate and into the bone. The heads of the screws are polyaxially mounted in the socket portions and as such may be inserted into the bone at a variety of angles. The socket portions of the coupling elements have slots in them which permit crush locking of the heads of the screws once the sockets seat and are forceably driven into the tapered portions of the corresponding holes. The cap portions are threaded so they may be advanced into the upper portions of the corresponding holes, thereby further locking the coupling elements into the holes, and applying an additional driving force against the corresponding socket portions to crush lock the screw heads at the selected angle relative to the plate.

7 Claims, 8 Drawing Sheets ns 5,607,426

THREADED POLYAXIAL LOCKING SCREW PLATE ASSEMBLY

CROSS-REFERENCE TO RELATED APPLICATION

This application is a continuation-in-part of application U.S. Ser. No. 08/421,087, entitled "Anterior Spinal Polyaxial Locking Screw Plate Assembly", filed Apr. 13, 1995, now U.S. Pat. No. 5,520,690.

BACKGROUND OF THE INVENTION

1. Field of the Invention

This invention relates generally to a spinal implant assembly for holding adjacent vertebral bones fixed. More particularly, this invention relates to a novel assembly of bone screws and plates for use in surgical procedures for stabilizing the relative motion of, or permanently immobilizing, vertebral bodies, wherein the screws form a polyaxial coupling of the plate to the bone, and which maintains a flush exterior plate surface through a wide range of entrance angulation.

2. Description of the Prior Art

The bones and connective tissue of an adult human spinal column consists of more than 20 discrete bones coupled sequentially to one another by a tri-joint complex which consist of an anterior disc and the two posterior facet joints, the anterior discs of adjacent bones being cushioned by cartilage spacers referred to as intervertebral discs. These more than 20 bones are anatomically categorized as being members of one of four classifications: cervical, thoracic, lumbar, or sacral. The cervical portion of the spine, which comprises the top of the spine, up to the base of the skull, includes the first 7 vertebrae. The intermediate 12 bones are the thoracic vertebrae, and connect to the lower spine comprising the 5 lumbar vertebrae. The base of the spine is the sacral bones (including the coccyx). The component bones of the cervical spine are generally smaller than those of the thoracic spine, which are in turn smaller than those of the lumbar region. The sacral region connects laterally to the pelvis. While the sacral region is an integral part of the spine, for the purposes of fusion surgeries and for this disclosure, the word spine shall refer only to the cervical, thoracic, and lumbar regions.

Referring now to FIGS. 1 and 2, a typical vertebral body is shown in a top view and a side view. The spinal cord is housed in the central canal 10, protected from the posterior side by a shell of bone called the lamina 12. The lamina 12 has three large protrusions, two of these extend laterally from the shell and are referred to as the transverse process 14. The third extends back and down from the lamina and is called the spinous process 16. The anterior portion of the spine comprises a set of generally cylindrically shaped bones which are stacked one on top of the other. These portions of the vertebrae are referred to as the vertebral bodies 20, and are each separated from the other by the intervertebral discs 22. Pedicles 24 are bone bridges which couple the anterior vertebral body 20 to the corresponding lamina 12 and posterior elements 14, 16.

The spinal column of bones is highly complex in that it includes over twenty bones coupled to one another, housing and protecting critical elements of the nervous system having innumerable peripheral nerves and circulatory bodies in close proximity. In spite of these complications, the spine is a highly flexible structure, capable of a high degree of curvature and twist in nearly every direction.

Genetic or developmental irregularities, trauma, chronic stress, tumors, and disease are a few of the causes which can result in spinal pathologies for which permanent immobilization of multiple vertebrae may be necessary. A variety of systems have been disclosed in the art which achieve this immobilization by implanting artificial assemblies in or on the spinal column. These assemblies may be classified as anterior, posterior, or lateral implants. As the classification suggests, posterior implants are attached to the back of the spinal column, generally hooking under the lamina and entering into the central canal, attaching to the transverse process, or coupling through the pedicle bone. Lateral and anterior assemblies are coupled to the vertebral bodies.

The region of the back which needs to be immobilized, as well as the individual variations in anatomy, determine the appropriate surgical protocol and implantation assembly. The use of screw plate assemblies for stabilization and immobilization via lateral or anterior entrance is, however, common.

Because the spine is routinely subject to high loads which cycle during movement, one of the primary concerns of physicians performing spinal implantation surgeries, as well as of the patients in whom the implants are placed, is the risk of screw pull-out. Screw pull-out occurs when the cylindrical portion of the bone which surrounds the inserted screw fails. A bone screw which is implanted perpendicular to the plate is particularly weak because the region of the bone which must fail for pull-out to occur is only as large as the outer diameter of the screw threads. It has been found that for pull-out to occur for a pair of screws which are angled inward, "toe nailed", or ones which diverge within the bone, the amount of bone which must fail increases substantially as compared to pairs of screws which are implanted in parallel along the axis that the loading force is applied. It has, therefore, been an object of those in the art to provide a screw plate assembly which permits the screws to be entered into the vertebral body at angles other than 90 degrees.

A great concern, however, with screws being implanted in the anterior portion spine, most particularly in the cervical spine, is that their are important internal tissue structures which, because of their proximity to the implant, may be damaged by a dislocated screw. In the cervical spine, the esophagus is located directly in front of the anterior surface of the vertebral body, and therefore, in potential contact with an implanted cervical plate. Breaches of the esophageal wall permit bacterial contamination of the surrounding tissues, including the critical nerves in and around the spinal cord. Such contamination can be fatal. Because screw pull-out represents one of the largest risks of esophageal perforation, it has been an object of those in the art to produce a cervical screw plate design having a locking means which couples, not only the plate to the bone, but locks the screw to the plate. In such a design, it is intended that, even if the bone holding the screw fails, the screw will not separate from the plate.

In addition to pull-out, however, it has been observed that if the screw plate design includes screw heads which protrude beyond the exterior surface of the plate, long term wearing of surrounding tissues may occur, leading to the development of abscesses and holes, which, once again, can have grave consequences. With respect to cervical plates, which are necessarily thin, on the order of a few millimeters, unless the system is designed to specifically accommodate non-perpendicular screw-in directions, the heads of the screws which are desirably toe-nailed in are a considerable risk.

Similar concerns exist in the thoracic and lumbar regions with respect to anterior and lateral fixation implants as their are proximally located organs as well as a plurality of major blood vessels which may be compromised by either catastrophic screw pull-out and/or long term wearing of non-flush surface protrusions.

One screw plate design which has been offered to provide physicians and patients with a reduced risk of pull-out or damage to proximal tissues is the Orion (Reg. Trademark) Anterior Cervical Plate System of Sofamor Danek USA, 1800 Pyramid Place, Memphis, Tenn. 38132. The Orion$_{TM}$ system teaches a plate having two pair of guide holes through which the screws are inserted to fix the plate to the vertebral body. The plate further includes external annular recessions about each of the guide holes which are radially non-symmetric in depth. More particularly, the annular recessions serve as specific angle guides for the screws so that they may be inserted non-perpendicularly with respect to the overall curvature of the plate. In addition, the Orion$_{TM}$ plate includes an additional threaded hole disposed between each of the pairs of guide holes so that a corresponding set screw may be inserted to lock the bone screws to the plate.

Although the Orion$_{TM}$ system achieved certain advantages over prior cervical screw plate assemblies, it is not without failures. Specifically, a given plate can accommodate only one screw-in angulation per hole, preferably in accordance with the angle of the annular recession. This is undesirable, in that physicians often must inspect the vertebral bodies during the implantation procedure before making the decision as to which screw-in angle is the ideal. By forcing the physician to chose from a limited set of angles, it is unavoidable that physicians will be forced to implant plates having screws which were positioned non-ideally. While providing a variety of plates having different angle guide holes and annular recession orientations is possible, the complexity and expense of providing a full spectrum of plates available in the operating room for the surgeon to choose from is undesirable. It is a failure of the system that one plate cannot accommodate a variety of different screw-in angles.

It is further a failure of the Orion$_{TM}$ system that an extra set screw is required to lock the screw to the plate. Plates for use in the cervical spine are very thin, and if the screw head already rests in an annular recess, and there is to be enough room for the head of the set screw to rest on top of the head of the bone screw, the thickness of the remaining plate must be reduced even further. The thinner the plate is at the load bearing points—the guide holes—the weaker the plate is overall.

While the preceding discussion has focused on a specific cervical screw plate system and its failures, the same failures apply to the art of vertebral immobilizing screw plate systems which are presently available as well. There are no presently available screw plate assemblies which present a flush surface and provide for means of preventing both screw pull-out from the bone and screw backout from the plate, while simultaneously providing for a wide range of angulation for the bone screws.

An additional concern for physicians who implant screw plate assemblies for spinal fixation is proper alignment for pre-drilling of the holes into which the bone screws are driven to hold the plate. As suggested above with respect to the angulation of the annular recesses of the Orion$_{TM}$ system, the process of forming the holes generally involves placing the plate against the appropriate vertebral bodies and using a guide to hold the proper angle with respect to the plate and bone as a drill is used. The difficulty in this process involves slippage at the interface between the unsecured plate and the bone. To avoid slippage, the surgeon is generally required to use, simultaneously, a plate holding mechanism, which may be removable affixed to the plate, to maintain the plate in its proper position, a drill guide to set the desired angulation (which is set by the thread angle of the plate), and the drill itself. It is understood that simultaneous manipulation of these three tools by the surgeon is tedious and difficult.

It is therefore, an object of the present invention to provide a new and novel cervical, thoracic, and/or lumbar screw plate design having a polyaxial coupling of the screw to the plate, whereby a single plate is compatible with a wide range of screw-in angles.

It is also an object of the present invention to provide a screw plate design having a flush exterior while being fixed to the vertebral bodies which it immobilizes; having no screw head protrusion despite non-perpendicular angulation.

It is also an object of the present invention to provide a spinal insert assembly which is more sturdy and more versatile than previous designs.

Further, it is an object of the present invention to provide a screw plate design which provides the surgeon with the greatest freedom to choose the most desirable angle to direct the bone screw.

It is also an object of the present invention to provide an orthopedic screw plate assembly which has a simple and effective locking mechanism for locking the bone screw to the plate.

It is also an object of the present invention to provide a screw plate assembly which has a simple and effective means of holding the plate in position for the pre-drilling of screw holes.

Other objects of the present invention not explicitly stated will be set forth and will be more clearly understood in conjunction with the descriptions of the preferred embodiments disclosed hereafter.

SUMMARY OF THE INVENTION

The preceding objects of the invention are achieved by the present invention which is a flush locking polyaxial screw plate assembly for use in stabilizing and immobilizing vertebral bodies. The assembly comprises a plate having a set of holes which are threaded at one end and tapered at the other, bone screws having a semi-spherical top portion, and a two-part coupling element. The top piece of the coupling element has an external threading for locking with the threaded end of the holes in the plate, and also has an interlocking mechanism for joining with the lower piece of the coupling element. The lower piece of the coupling element has a semi-spherical interior volume, which is expandable and contractable, for receiving the semi-spherical head of the screw therein. The bottom portion of the lower piece of the coupling element further includes an exterior taper which mates with the tapered end of the corresponding hole in the plate, so that there is an inwardly directed force applied to the lower piece, thereby causing the interior volume of the coupling element to contract and lock to the head of the screw.

The present invention has a preferred embodiment which is summarized hereinbelow. The plate is a flat metal element, having a generally planar shape with rounded corners, contoured to the curved cylindrical surface of the vertebral bodies to which it is to be secured. There are four holes disposed in pairs at distal ends of the plate. The holes extend through the plane of the plate and are positioned so that they are aligned in pairs with the vertebral bodies to which the plate is to be attached. The top portions of the holes have a constant diameter and are threaded. The lower portions of the holes are tapered inwardly and are smooth.

The shaft portion of the bone screws may be of a variety of standard designs, or a particular design which may be found more secure than standard ones. The head, however, is not standard in that it comprises a semi-spherical section. For the purposes of inserting the screw into the bone, the head comprises a recessed region, such as a slot, cross (phillips), star, or hexagon, which is ideally suited for mating to an appropriate screwdriving tool. The recess, however, shall not alter the exterior radially semi-spherical shape of the head.

The two part coupling element comprises and socket portion and a cap portion. The socket portion is designed with an interior semi-spherical volume, so that it may receive the semi-spherical head of a corresponding bone screw. The interior volume of the socket portion is open at both axial ends thereof. The exterior surface of the socket portion, at the bottom thereof, includes a first set of slots which extend upwardly from the opening so that the interior semi-spherical volume may be expanded or contracted by the application of a radial force. In addition, the exterior surface at the bottom is tapered so that it is narrower at the bottom than at a midpoint.

The upper exterior surface of the socket portion comprises a second set of slots, directed axially along the element to the midpoint, such that the upper opening of the socket element may expand and contract in accordance with the application of a radial force thereon. The exterior surface of this upper section of the socket portion is not tapered and is narrower than the widest taper position of the bottom of the socket portion. The upper section, however, does further include an outwardly extending annular lip at the uppermost axial position. This upper section is designed to be inserted into, and joined with, the cap portion of the coupling element.

The cap portion has a generally cylindrical shape, having an open bottom. The open bottom is inwardly tapered, forming an inwardly extending annular lip, so that as the upper end of the socket portion is inserted, its upper slots are narrowed. Once axially inserted beyond this taper, the upper section of the socket portion expands outward over the inwardly extending annular lip. The inwardly extending annular lip engages the outwardly extending lip of the socket portion so as to prevent disengagement of the two pieces. The socket portion is then permitted to slide into the cap portion, until the larger diameter of the tapered lower portion of the socket contacts the entrance of the cap portion.

The exterior surface of the cap portion is threaded, so that it may engage the threading of the upper portion of the corresponding hole. In addition, the top of the cap includes an opening so that a screw driving tool may directly engage the top of the screw.

The first step in the process of implanting this embodiment of the invention is to assemble the parts described above. (It is intended that this assembly occur at the manufacturing site, and not be the responsibility of the surgical staff.). The semi-spherical head of the screw is inserted into the interior volume of the socket portion, and held in place by the interference fit of the maximum diameter of the head with the unexpanded openings at the top and bottom of the element. The head is inserted from the bottom, and more specifically by applying a pressure which causes the bottom opening to expand to receive the head into the volume.

Once the screw head is inserted, the upper end of the socket portion is inserted into the opening of the cap portion. This insertion causes the top of the socket portion to contract inward slightly until the annular lips of each portion engage one another. The socket portion and the cap portion are thereby joined loosely so that each may slide and rotate relative to one another.

The surgeon then positions the plate against the vertebral bodies and aligns the entry points for the screws. The next step is to pre-drill the holes into the bones at the desired angle, into which the screws will be inserted. With the plate in place, the screws (with the corresponding socket and cap portions in place on the head of each screw) are inserted through the holes of the plate, and into the vertebral bodies. The coupling element provides access to the screw head for driving it into the bone. At all times during this insertion, the head of the screw is loosely retained within the coupling element, so that the coupling element may polyaxially angulate relative to the screw, within a range of angles defined by the diameter of the neck of the screw and the bottom opening of the socket portion.

As the screw is inserted into the bone, at the desired angle, the socket portion of the coupling element angulates so that the tapered bottom portion thereof seats into the tapered bottom of the hole in the plate. Continued driving of the screw into the bone, and therefore the socket portion of the coupling element deeper into the tapered hole, causes the first set of slots in the bottom end of the socket portion to narrow, thus causing the head of the screw to be crush locked to the coupling element. The cap portion of the coupling element is then threadably inserted into the hole, locking the coupling element in the hole, and further driving the socket portion into the hole.

In a preferred variation of this embodiment, the interior surface of the cap portion includes a slight narrowing taper so that as the cap is threaded downward into the hole in the plate, the upper slots of the socket portion are also narrowed, further increasing the crush locking effect on the head of the screw.

BRIEF DESCRIPTION OF THE DRAWINGS

FIG. 3b is a side cross-section view of one hole of the locking plate shown in FIG. 3a.

DETAILED DESCRIPTION OF THE PREFERRED EMBODIMENT

While the present invention will be described more fully hereinafter with reference to the accompanying drawings, in which particular embodiments are shown, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the present invention and not as limiting of such broad scope. Like numbers refer to similar features of like elements throughout.

Referring now to FIG. 3s a plate which is an element of the present invention is shown in a perspective view. The plate 100 may be constructed of any suitably biocompatible material which has the structural strength and durability to withstand the cyclical loading associated with long term fixation to the spine. Materials which would be suitable for such applications include titanium alloys and steels. A specific titanium material which has been utilized in implants of the prior art include ASTM F-136 titanium alloy (Ti 6AL-4V). This material has enhanced mechanical properties including fatigue endurance and tensile strength, as compared with pure titanium.

Figure 2:
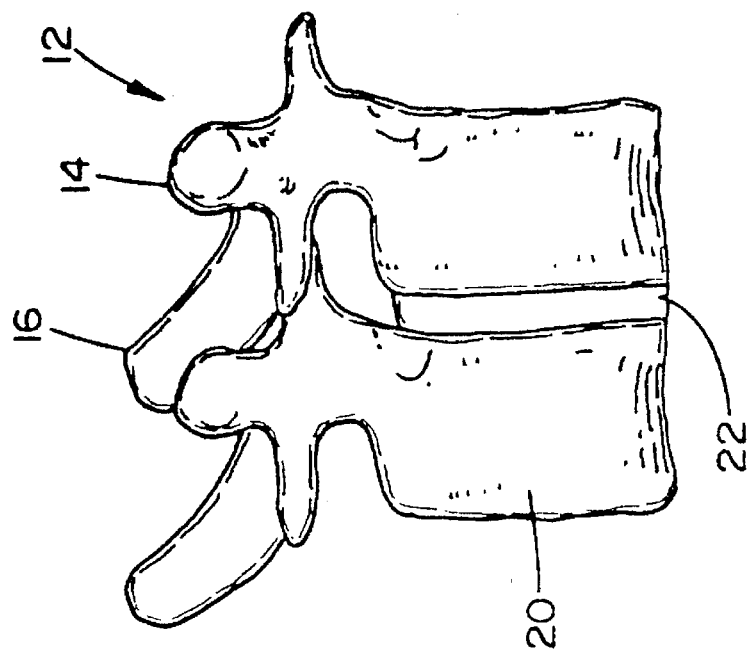
FIG. 2 is a side view of sequentially aligned vertebral bones.
Figure 1:
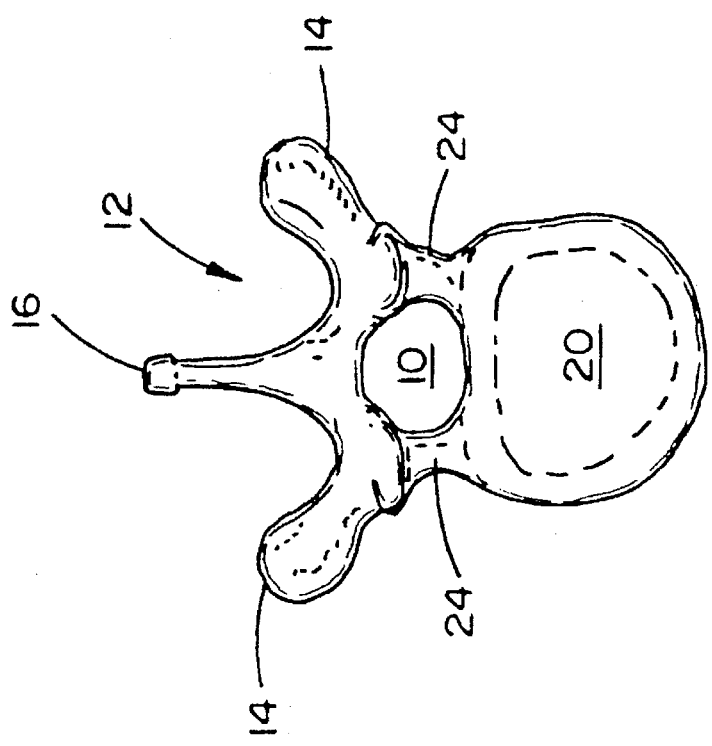
FIG. 1 is a top view of a vertebral bone, the stabilization of which the present invention is directed.
Figure 3A:
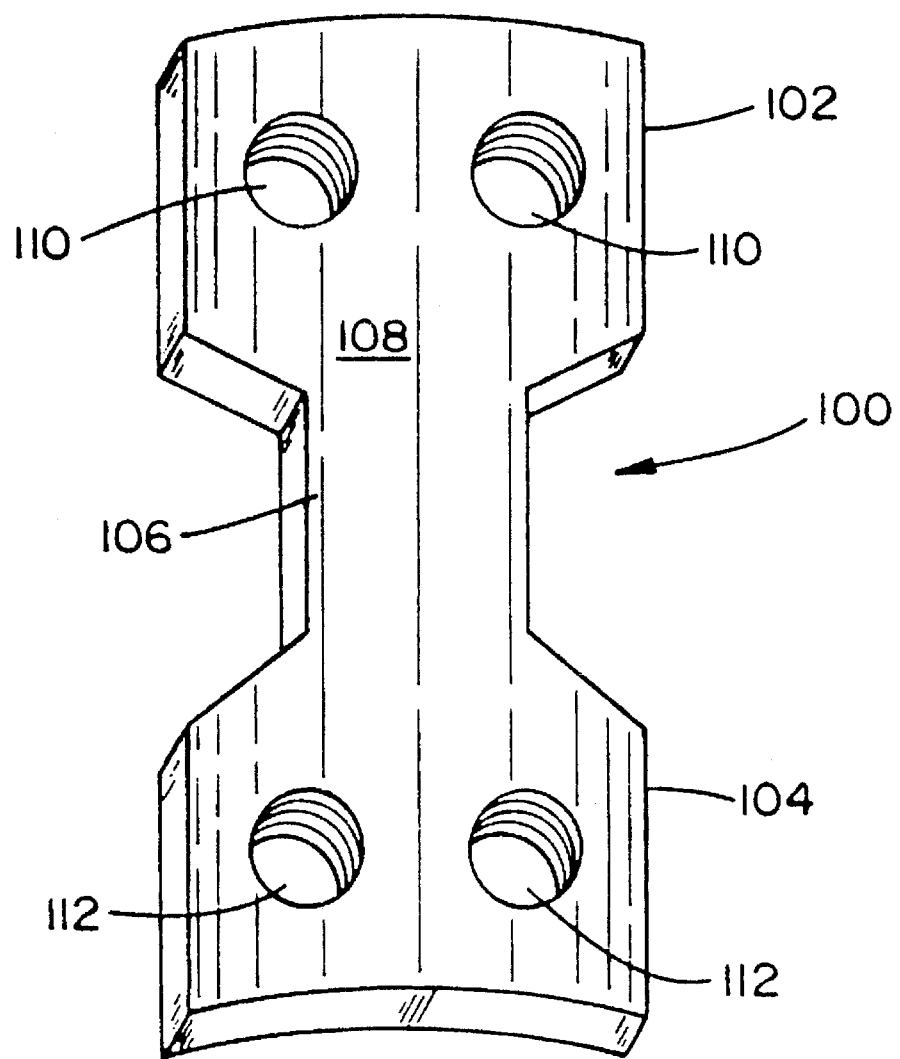
FIG. 3a is a perspective view of a locking plate which is an element of one aspect of the present invention.

The plate 100 comprises upper and lower portions 102, 104 respectively, which are connected by a narrower region 106, therein being generally I-shaped. It shall be understood that a variety of conformations may be utilized in the alternative, the I-shape being the most illustrative for the purpose of description. The plate 100 also has a top surface 108 and a bottom surface (not shown). A slight curvature is imparted to the plate 100 so that it may grossly conform to the cylindrical morphology of the vertebral bodies which it couples. As shown in FIG. 3a, the top surface 108 is the convex surface, the bottom surface (not shown) is concave.

Two pairs of holes 110 and 112, which extend fully through the plate, from the upper surface 108 through the lower surface, are disposed in the upper and lower portions 102, 104 respectively. Each of the holes 110, 112 is ideally suited for receiving therethrough a bone screw for affixing the plate to the vertebral bodies.

Figure 3B:
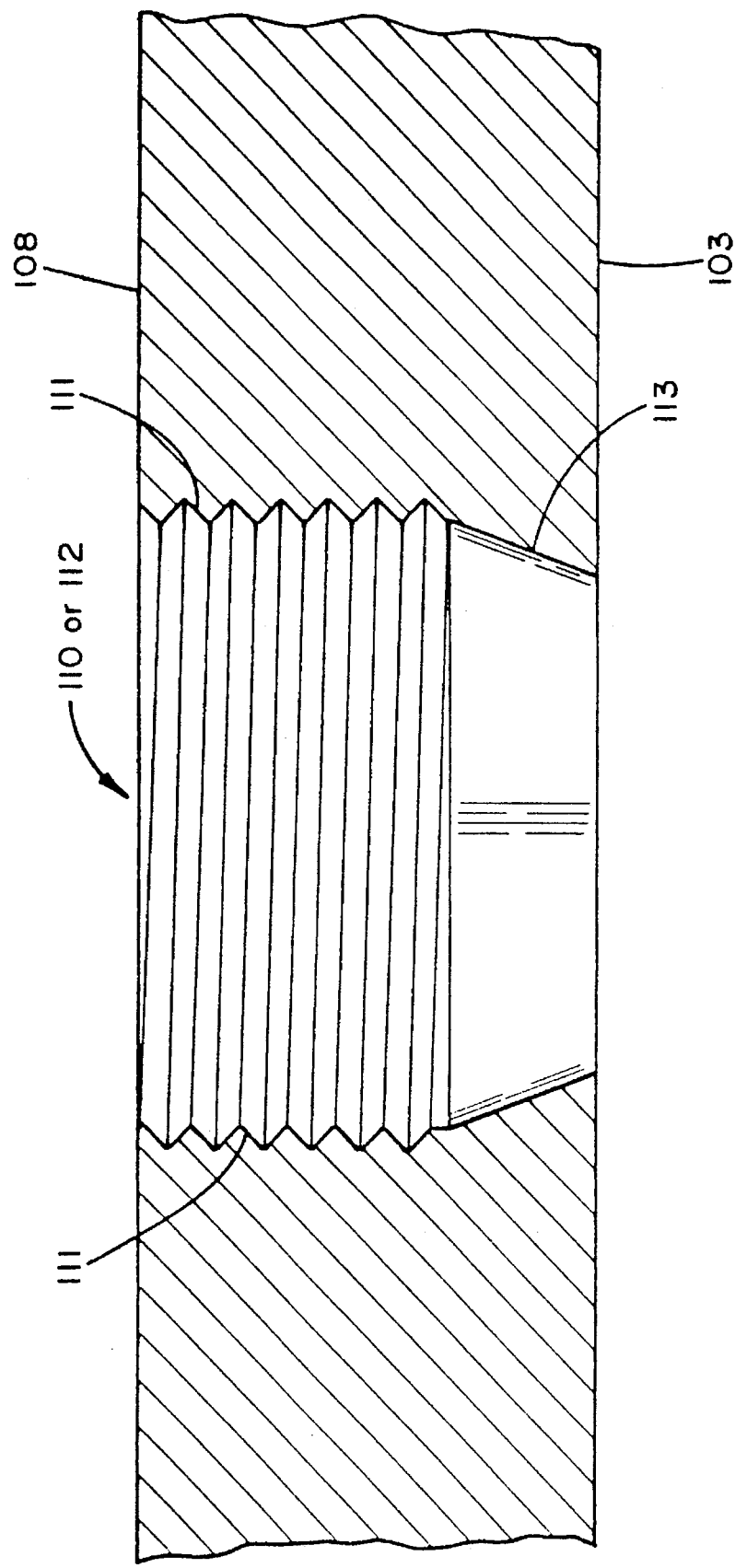

Referring now to FIG. 3b, in which a side cross-section view of a hole, 110 or 112, is shown, the interior conformation of the hole is illustrated. Extending from the top surface 108 of the plate, into the hole 110 or 112, to a position which is above the bottom surface 103 is a threading 111. The diameter of the hole 110 or 112 does not vary in the threaded region, however, the bottom section of the hole 110 or 112 includes an inward taper 113.

Figure 4:
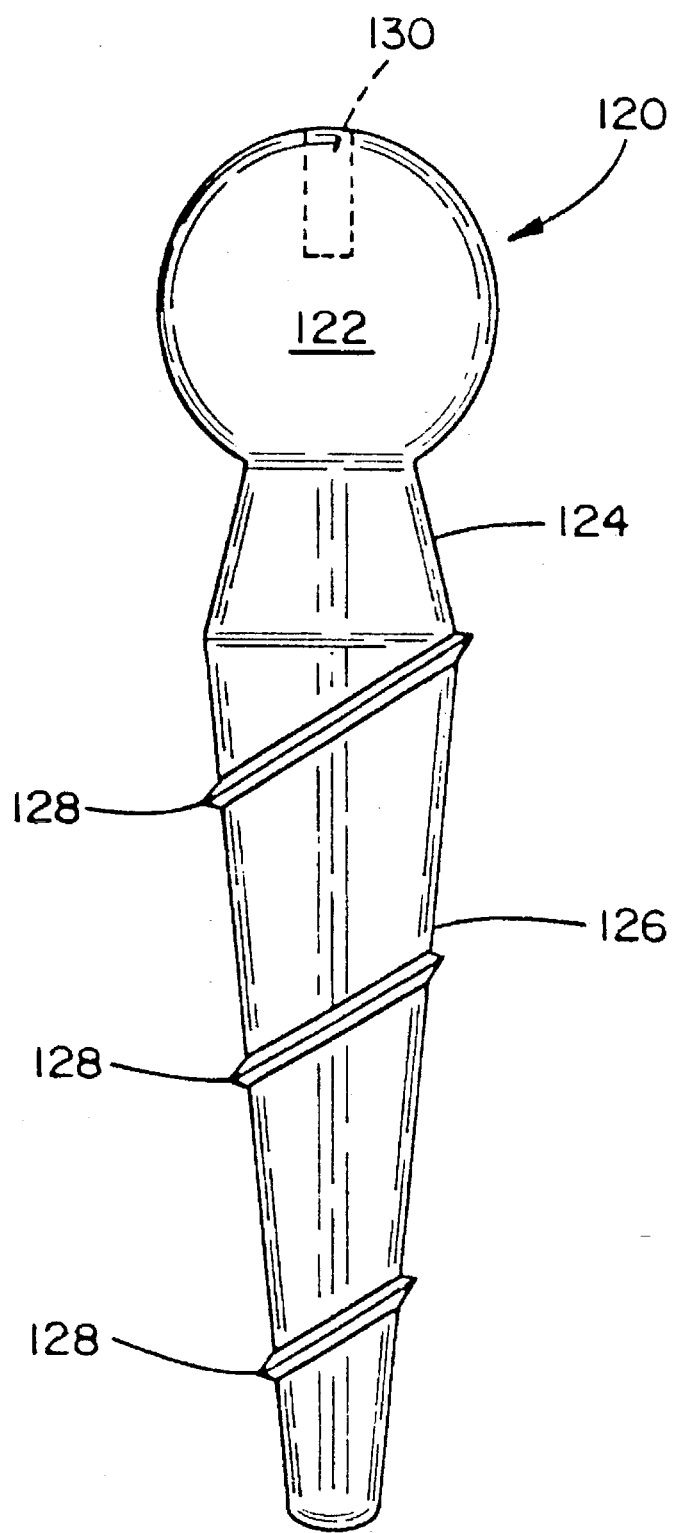
FIG. 4 is a perspective view of a bone screw which is an element of one aspect of the present invention.

Referring now also to FIG. 4, a screw of a type which is ideally suited for coupling the plate 100 to vertebral bones is shown in a side view. The screw 120 comprises a head portion 122, a neck 124, and a shaft 126. In FIG. 4, the shaft 126 is shown as having a tapered shape with a high pitch thread 128. It shall be understood that a variety of shaft designs are interchangeable with the present design. The specific choice of shaft features, such as thread pitch, or shaft diameter to thread diameter ratio, or overall shaft shape, etc. should be made be the physician with respect to the conditions of the patient's bone, however, this invention is compatible with a wide variety of shaft designs.

The head portion 122 of the screw 120 comprises a semi-spherical shape, which has a recess 130 in it. It is understood that the semi-spherical shape is necessarily is a section of a sphere, greater in extent than a hemisphere, and exhibits an external contour which is equidistant from a center point of the head. In a preferred embodiment, the major cross-section of the semi-spherical head 122 (as shown in the two dimensional illustration of FIG. 4) includes at least 270 degrees of a circle.

The recess 130 defines a receiving locus for the application of a torque for driving the screw 120 into the bone. The specific shape of the recess 122 may be chosen to cooperate with any suitable screwdriving tool. For example, the recess 130 may comprise a slot for a flat-headed screwdriver, a crossed recess for a phillips head screwdriver, or most preferably, a hexagonally shaped hole for receiving an allen wrench. It is further preferable that the recess 130 be co-axial with the general elongate axis of the screw 120, and most particularly with respect to the shaft 126. Having the axes of the recess 130 and the shaft 126 co-linear facilitates step of inserting the screw 120 into the bone.

The semi-spherical head portion 122 is connected to the shaft 126 at a neck portion 124. While it is preferable that the diameter of the shaft 126 be less than the radius of the semi-spherical head 122, it is also preferable that the neck 124 of the screw 120 be narrower than the widest portion of the shaft 126. This preferable dimension permits the screw to be inserted at a variety of angles while still permitting the coupling element (as described with respect to FIGS. 5 and 6) to be screwed into the appropriate hole 110 or 112 of the plate 100 and remain coupled to the head 122.

Figure 5:
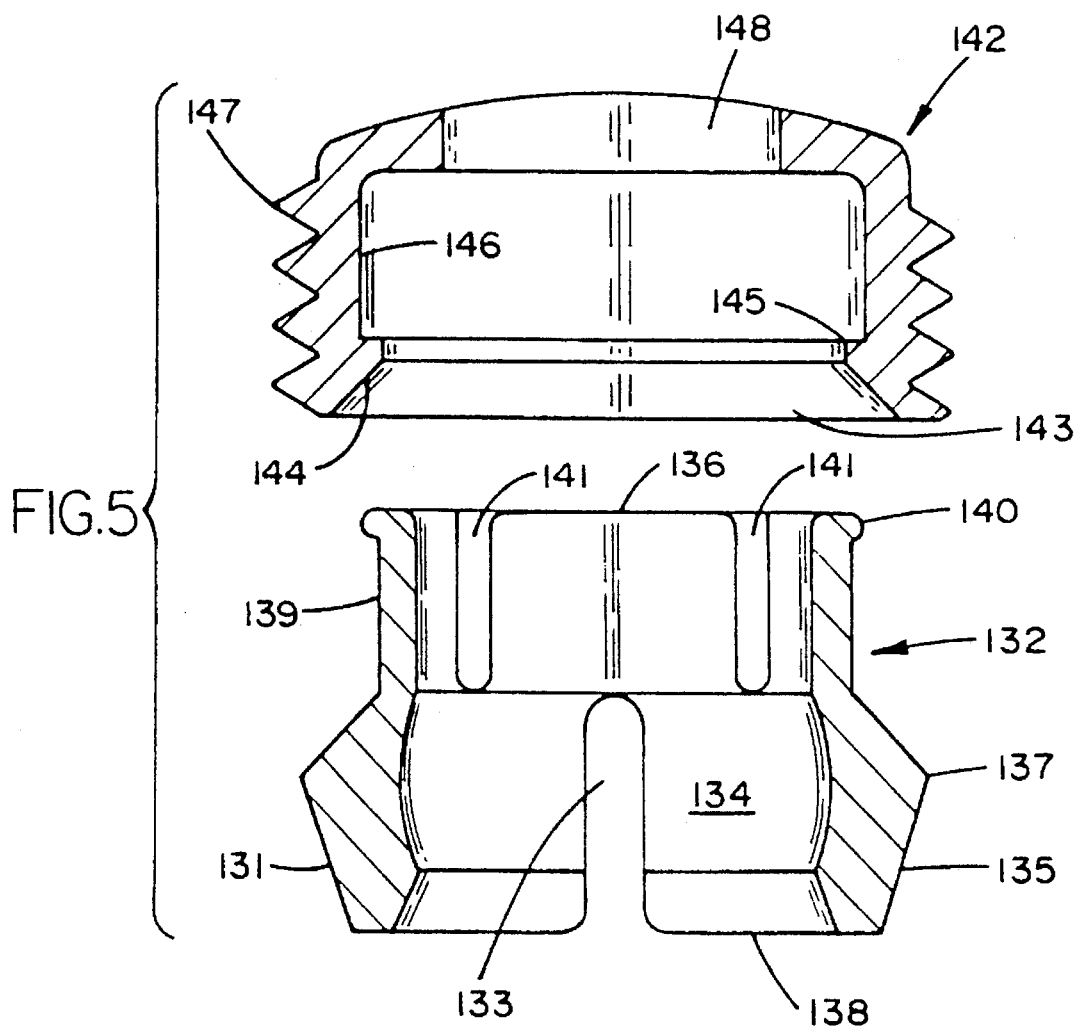
FIG. 5 is a side cross-section view of the disassembled two-part coupling element, and more specifically of the socket portion and cap portion which are aspects of and embodiment of the present invention.

Referring now to FIG. 5, the two portions which form the coupling element of the present invention are shown in a side cross-section view. Phantom lines show the interior structure of the elements along the diametrical cross section. With specific reference to the socket portion 132, the coupling element comprises a roughly cylindrical shape having an interior volume 134 in which the semi-spherical head 122 of the screw 120 is disposed. The interior volume 134 is open at the top 136 of the socket portion 132 and at the bottom thereof 138. The lower section 131 of the socket portion 132 comprises a set of slots 133 which extend vertically from the bottom 138 of the socket portion 132 to a position above the maximum diameter of the semi-spherical interior volume 134. These slots 133 permit the interior volume to expand and contract in accordance with the application of a radial force thereon. The external surface 135 of the lower section 131 of the socket portion 132 is tapered such that the narrowest part of the lower section 131 is at the bottom 138.

The upper section 139 of the socket portion 132 has a generally constant diameter, which is less than the diameter at the uppermost position 137 of the taper of the lower section 131. A second set of vertical slots 141 are provided in this upper section 139 so that it may also expand and contract in accordance with radial forces applied thereto. In addition, the uppermost end of this upper section 139 comprises an outwardly extending annular lip 140.

The cap portion 142 of the coupling element comprises an opening 143 in the bottom thereof, having an inwardly tapered entrance surface conformation 144. As the upper section 139 of the socket portion 132 is inserted into the opening 143 in the cap portion 142, the taper 144 of the opening 143 provides an inwardly directed force which causes the upper section 139 to contract (causes the slots 141 to narrow). This tapered entrance 144 opens to form an annular lip 145 which is useful for engaging and retaining the annular lip 140 of the upper section 139 of the socket portion 132. The interior surface 146 of the cap portion has a constant diameter, therein permitting the inserted upper section 139 of the socket portion 132 to slide and rotate relative to the cap portion 142.

The exterior surface of the cap portion 142 comprises a threading 147 which is designed to engage the threading 111 in the upper portion of the corresponding hole 110 or 112. In addition, the cap portion 142 comprises an axial hole 148 through which a surgeon may insert a screw driving tool to access the head of the screw which is positioned in the interior volume 134 of the socket portion 132.

Figure 6:
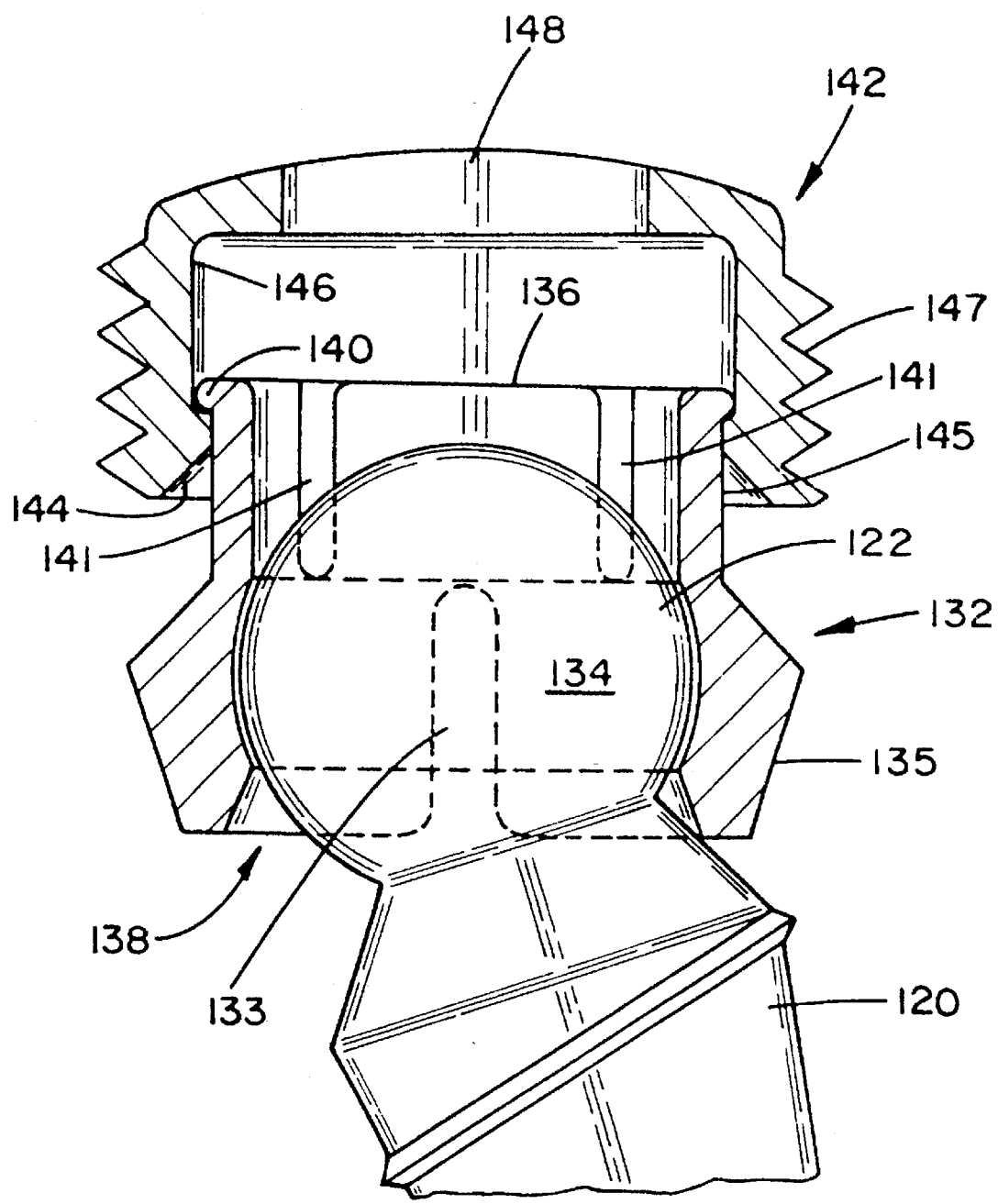
FIG. 6 is a side cross-section view of the assembled socket and cap portion of the two-part coupling element shown in FIG. 5, wherein the head of the screw shown in FIG. 4 has been inserted into the socket portion in accordance with an aspect of the present invention.

More particularly, with respect to the disposition of the head 122 of the screw 120 in the socket portion 132, and with reference to FIG. 6, a fully assembled coupling element is shown in a side cross-section view. The top 136 of the socket portion 132 is inserted into the opening in the cap portion 142 until the annular lip 140 of the socket 132 seats into the cap 142. The screw 120 is loosely held within the socket 132, which is, in turn, loosely retained within the cap 142.

Figure 7:
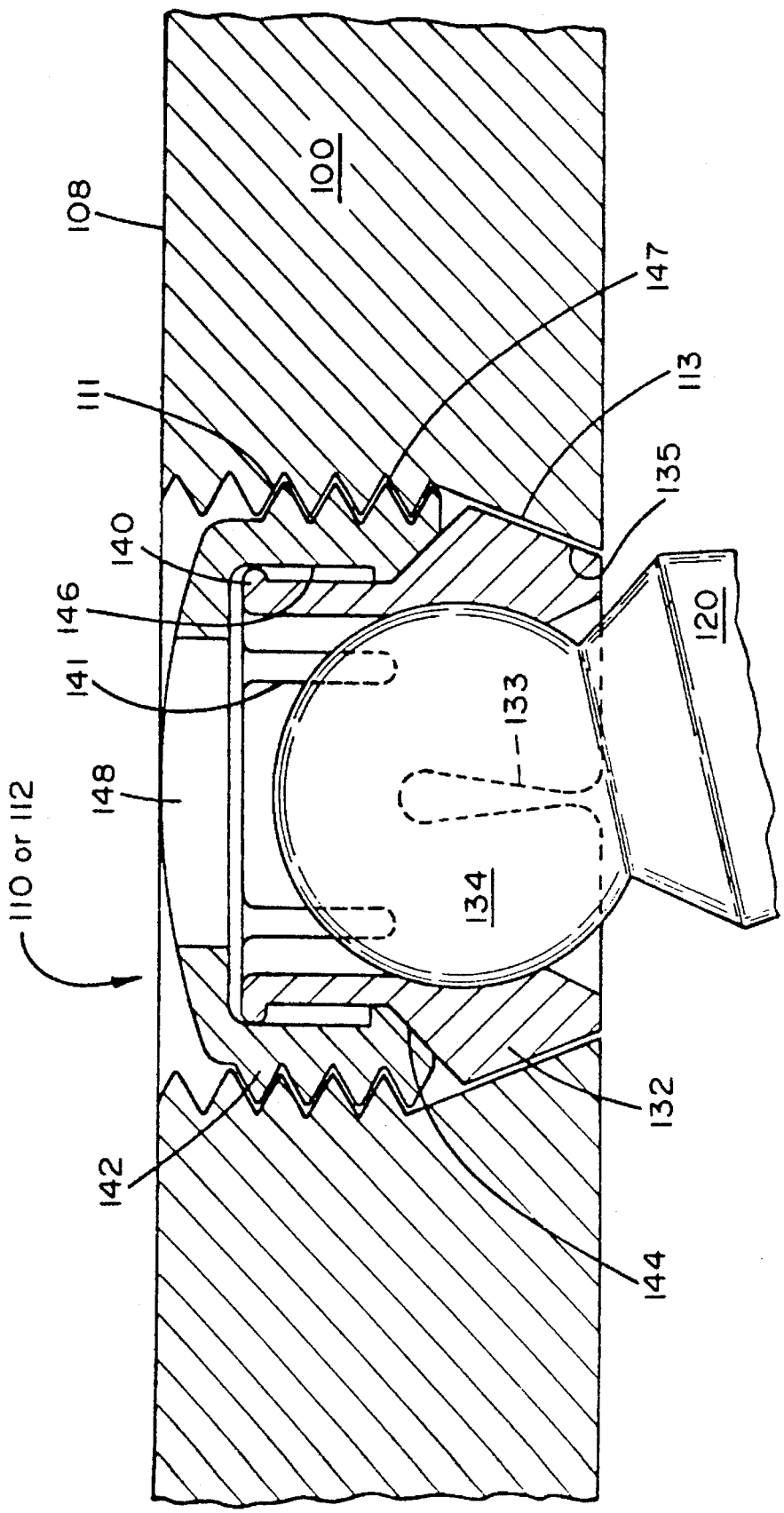
FIG. 7 is a side cross-section view of the inserted and fully locked plate, two-part coupling element, and screw in accordance with a preferred embodiment of the present invention.

Referring now to FIG. 7, in which the fully assembled and implanted plate, coupling element, and screw is shown in side cross-section view, the implantation of this embodiment is described. The plate 100 is positioned against the vertebral bones which are to be immobilized. A drill is used to pre-form holes into which the bone screws 120 are to be inserted (at the desired angulation). The screw 120 is then inserted and driven downward into the bone by use of the appropriate screw driving tool. As the screw 120 is driven deeper into the bone, the coupling element mounted to the head of the screw begins to enter the hole 110 or 112 of the plate 100. As the coupling element enters the hole 110 or 112, the tapered exterior surface 135 of the socket portion 132 seats against the tapered bottom 113 of the hole 110 or 112. Continued driving of the screw into the bone causes the slot 133 in the bottom of the socket portion 132 to narrow, thus causing the interior volume 134 of the socket portion 132 to crush against the head 122 of the screw 120.

The cap portion 142 of the coupling element may then be threadably advanced into the top section of the hole. As it is advanced, the upper annular lip 140 of the socket portion 132 slides upwardly along the inner surface 146 of the cap 142 until the bottom tapered opening 144 contacts the widened taper position of the socket portion 132. Continued advancement of the cap portion 142 provides further advancement of the socket portion 132 into the hole 110 or 112, thereby increased locking pressure within the interior volume 134 against the head 122.

Figure 8:
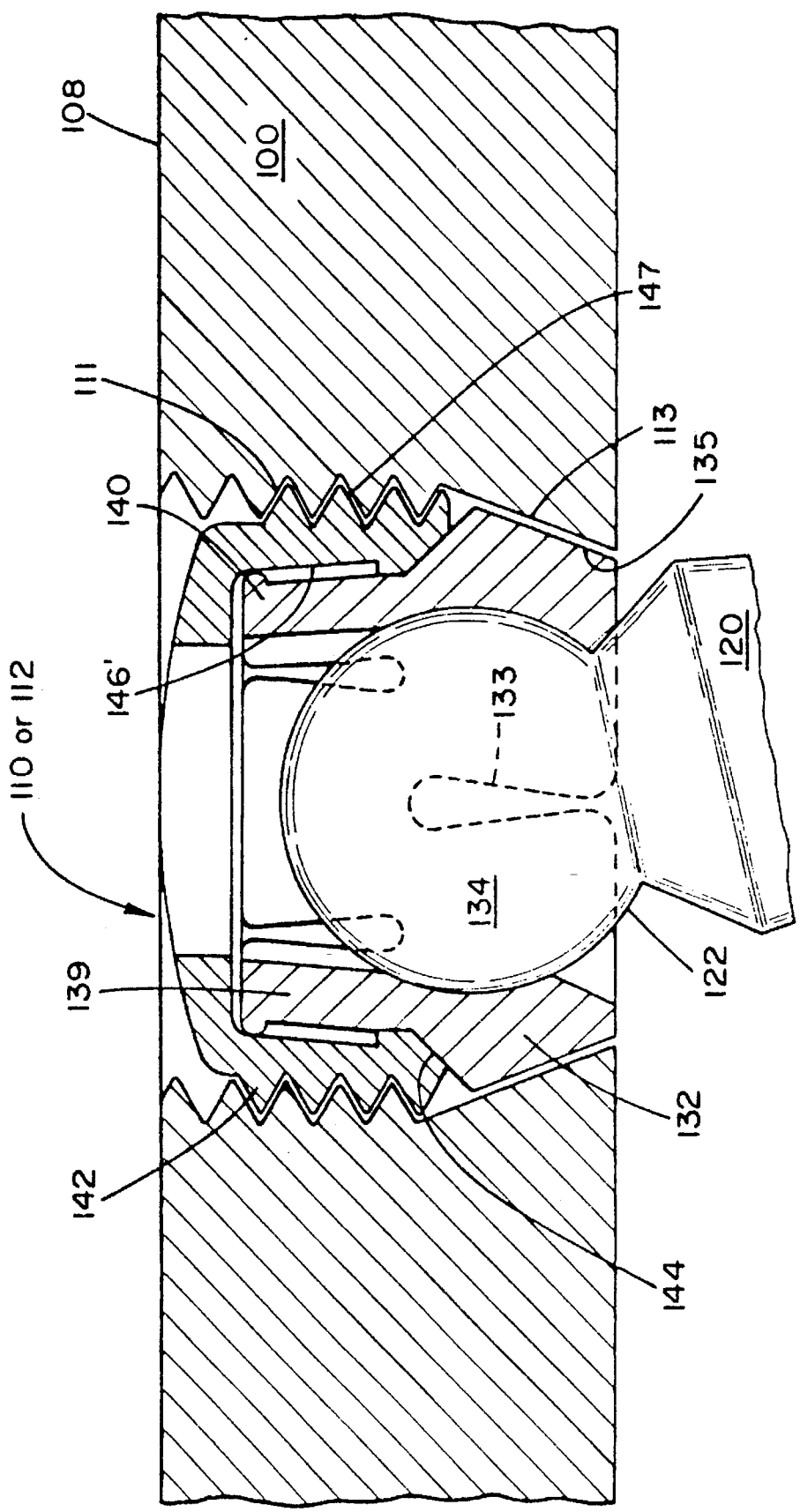
FIG. 8 is a side cross-section view of the inserted and fully locked plate, two-part coupling element, and screw in accordance with a highly preferred embodiment of the present invention wherein the cap portion includes a tapered interior surface.

Referring to FIG. 8, a variation of the above device is shown in a similar cross-section view. In this embodiment, the inner surface 146' of the cap portion 142 is tapered inwardly in the vertical direction so that the advancement of the cap portion 142 along the threading 111 of the hole 110 or 112 causes the annular lip 140 to be compressed inwardly. This causes the slots 141 of the upper section 139 of the socket portion 132 to narrow. This may be utilized to further clamp the interior volume 134 against the head 122 of the screw 120. Once screwed into the plate 100, and locked down, the cap portion 142 of the coupling element and the top surface of the plate 108 present a flush external surface.

While there has been described and illustrated implantation devices for stabilizing and immobilizing regions of the spine by affixing a polyaxial locking screw plate to the anterior portion of the vertebral bones, it will be apparent to those skilled in the art that variations and modifications are possible without deviating from the broad spirit and principle of the present invention which shall be limited solely by the scope of the claims appended hereto.

We claim:

1. A polyaxial locking screw plate assembly for the immobilization of vertebral bones, via fixation to surfaces thereof, comprising:

a plate having an upper portion and a lower portion, said upper and lower portions each having at least one through hole, each of said through holes having an upper threaded portion and a lower tapered portion;

a plurality of bone screws, each of said bone screws having a semi-spherical head portion and a shaft; and a plurality of coupling elements, each comprising a socket portion having a semi-spherical interior volume, upper and lower sections, and vertical slots formed on corresponding ones of said upper and lower sections, at least one of said slots rendering said interior volume expandable and contractable, said lower section having a tapered exterior surface for seating against the lower tapered portion of said corresponding through hole such that forceable advancement of socket portion into the tapered portion of the through hole causes the at least one of said slots to narrow whereby the semi-spherical interior volume contracts, and a cap portion having an opening in a bottom thereof and an interior chamber extending upwardly therefrom for joining with, and slideably retaining therein, the upper section of said socket portion, and exterior threading which is mateable with the threading of the corresponding hole, wherein said semi-spherical head portion is rotationally freely mounted within the semi-spherical interior volume of the socket portion of the coupling element prior to insertion, and whereby the insertion of the shaft of the bone screw and the coupling element into the corresponding through hole, and the insertion of said shaft of the bone screw into the vertebral bone at a selected angle within a predetermined range of angles including non-perpendicular angles to the plate, causes the tapered exterior surface of the socket portion to seat and to be forceably advanced against the tapered portion of the through hole such that the semi-spherical head of the screw is locked within the contracted semi-spherical interior volume, and whereby threaded advancement of the cap portion into said through hole provides additional forceable advancement of the socket portion against the tapered portion of the through hole.

2. The polyaxial locking screw plate assembly as set forth in claim 1, wherein said at least one through hole of each of said upper and lower portions of said plate comprises a pair of through holes.

3. The polyaxial locking screw plate assembly as set forth in claim 1, wherein the head portion of each of said screws comprises a recess to which a screwdriving tool is mateable for inserting said screw through the corresponding hole and into the vertebral bone.

4. The polyaxial locking screw plate assembly as set forth in claim 1, wherein said socket portion comprises an opening in said upper section thereof, through which a screwdriving tool may be inserted, and which may be aligned with the recess in the head of the screw.

5. The polyaxial locking screw plate assembly as set forth in claim 4, wherein said cap portion comprises an opening in a top thereof, aligned with the opening in the upper section of the socket portion, through which said screwdriving tool may be inserted, and which top surface recess may be aligned with the recess in the head of the screw.

6. The polyaxial locking screw plate assembly as set forth in claim 1, wherein said socket portion further comprises a substantially constant diameter upper section having an outwardly annular extending lip at an extreme end thereof, wherein said opening in the bottom of the cap portion comprises an inwardly directed annular lip, and wherein at least one of said vertical slots in the upper section of said socket portion renders the upper section thereof to be expandable and contractable such that the upper section of the socket portion may be forceably inserted into the opening in the bottom of the cap portion so that it may be retained in the interior chamber therein by mutual interference engagement of the inwardly directed annular lip of the cap portion and the outwardly extending annular lip of the socket portion.

7. The polyaxial locking screw plate assembly as set forth in claim 6, wherein the interior chamber of the cap portion comprises a tapered surface such that advancement thereof into the hole causes an inwardly directed force against the upper section of the socket portion, therein causing the at least one of said vertical slots in the upper section to narrow and causes the upper section to contract and further lock the head of the screw within the interior semi-spherical volume of the socket portion.

* * * * *